United States Patent [19]

Rusz

[11] Patent Number: 4,603,691
[45] Date of Patent: Aug. 5, 1986

[54] PULMONARY VENTILATOR-BELLOWS-ASSEMBLY KIT

[76] Inventor: Tibor Rusz, 761 West St., Pittsfield, Mass. 01201

[21] Appl. No.: 685,906

[22] Filed: Dec. 24, 1984

[51] Int. Cl.$^4$ ............................................. A61M 16/00
[52] U.S. Cl. ................................................. 128/205.15
[58] Field of Search ...................... 128/205.13, 205.14, 128/205.15, 204.28, 205.23, 728; 92/45, 128

[56] References Cited

U.S. PATENT DOCUMENTS 3,789,837  2/1974  Philips et al. .............. 128/205.15 X
3,841,327  10/1974  Hay .................................. 128/204.28

OTHER PUBLICATIONS

Advertisement, Anesthesiolocy News, Dec. 1982, p. 20, Ohio Medical Products—"Ohio 7000 Electronic Anesthesia Ventilator".

"Ventimeter Controller" by NARCO Air-Shields, two page brochure.

Primary Examiner—Kyle L. Howell
Assistant Examiner—Francis J. Jaworski
Attorney, Agent, or Firm—Arthur K. Hooks

[57] ABSTRACT

A pulmonary ventilator-bellows-assembly kit includes a base to which a large (adult) cylindrical housing and a small (pediatric) housing, either one of which are mountable and sealable to the same peripheral base portion. Also included are a large bellows mountable directly to the base and a small bellows that is mountable to the base via an adaptor. The cylindrical housings to base mounting means use a bayonet type lock and an O-ring seal so that mounting is simply and easily accomplished by inserting a housing and twisting it over the base. The small-bellows adaptor also seals to the base using an O-ring and the small housing automatically locks it into place. The adaptor is adapted to be stored on the base when the large bellows and large housing are mounted and in use.

12 Claims, 5 Drawing Figures

U.S. Patent   Aug. 5, 1986   Sheet 1 of 2   4,603,691
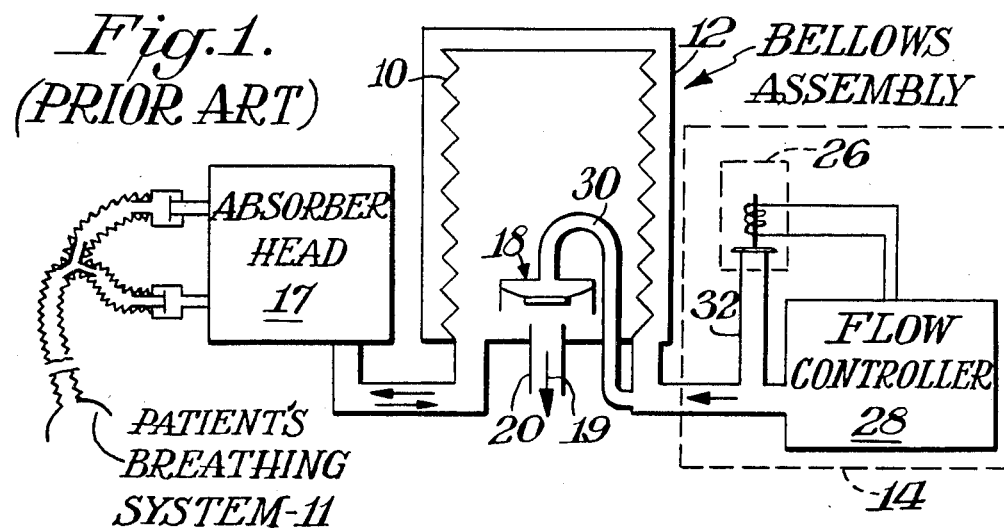
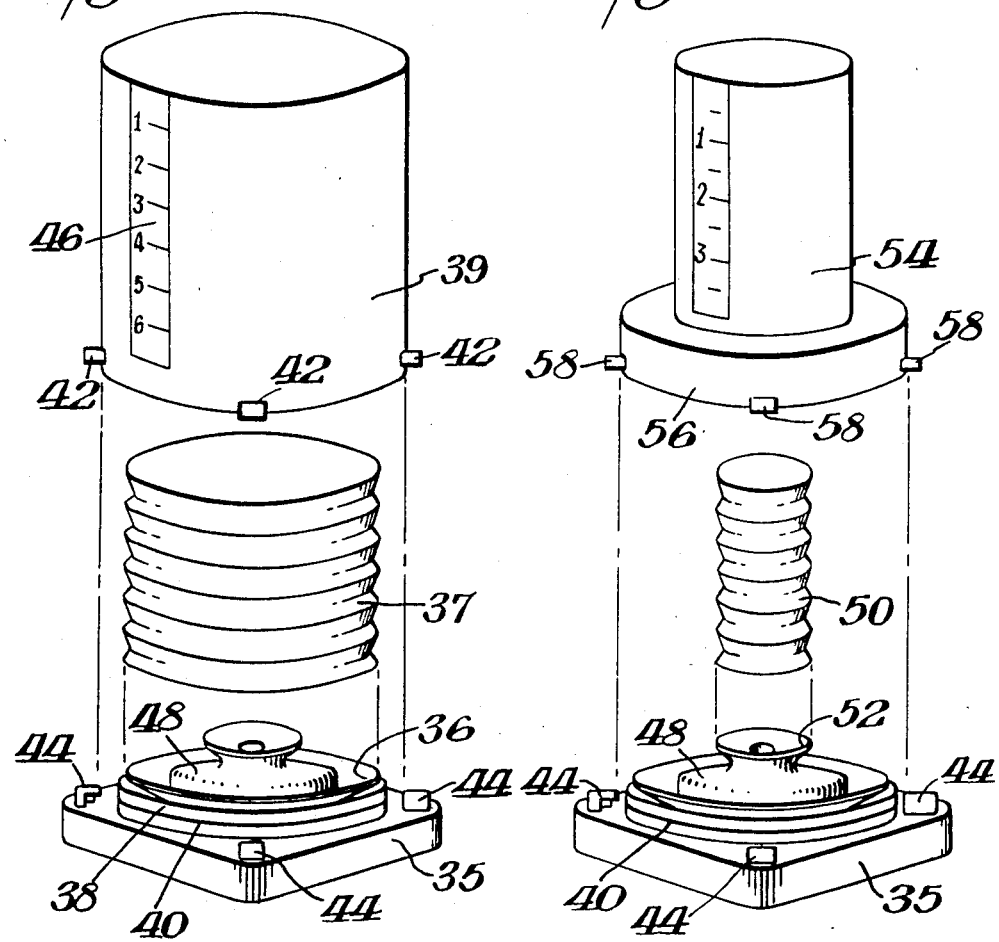

PULMONARY VENTILATOR-BELLOWS-ASSEMBLY KIT

BACKGROUND OF THE INVENTION

This invention relates to pulmonary-ventilator assemblies and more particularly to such assemblies in kit form capable of simple fast change over from large to small capacity ventilation modes, and visa versa.

Pulmonary-bellows-assemblies are typically used for forced ventilation of anesthetized human patients or animals undergoing surgery. The ventilating gas may contain carefully controlled amounts of oxygen, nitrous oxide or helium and must be kept sterile. Sterilization of the ventilation parts, like surgical instruments, is preferably accomplished by disassembly and subjecting the parts to steam but the plastic parts such as the plexiglass of commercial ventilators distort in steam and must be scrubbed with alcohol or other disinfecting agents.

In ventilation operation, the interior of the bellows 10 is connected to the patient's breathing system 11 as is illustrated in FIG. 1. The space between the bellows 10 and the surrounding bellows housing 12 is connected to the pneumatic driving control unit 14. The driving gas from the control unit 14 is usually air. During the inspiratory phase, the driving gas compresses the bellows 10 and forces the ventilating gas within the bellows 10 into the patient's breathing system 11. The absorber head 17 is a part of an anesthesia machine that removes the carbon dioxide from the exhaled gasses. During the expiratory phase the driving gas is released from the bellows housing 12 and the patient exhales into the bellows 10. When the bellows 10 reaches the maximum excursion, the pop-off valve 18 automatically opens and the excess breathing gas 19 escapes through the exhaust port 20.

The pressure over the upper surface of the valvediaphram 22 is always the same as that in the bellows housing 12 outside the bellows 10. The pressure acting on the lower surface of the diaphram 22 is always the same as the pressure within the bellows 10. The check valve 24 over exhaust port 20 is attached to the lower surface of the diaphram 22 and the pressure acting on the exhaustport side of the valve seat 24 is always ambient pressure.

During the inspiratory phase the driving gas exhaust valve 26 in the control unit 14 is closed and the driving gas generated by the flow controller 28 increases the pressure on the outside of the bellows 10. The driving gas is communicated to the top of the pop-off valve 18 via valve channel 30 and the pop-off valve 18 is held closed during the inspiratory phase. The driven pressure at the inside and outside of the bellows is the same.

During the expiratory phase the driving gas exhaust valve 26 opens dropping the pressure in pipe 32 to the ambient. The pressure outside the bellows drops, and the pressurized resilient lungs of the patient discharge back into the bellows 10 and when the bellows 10 becomes fully extended to or at the top of the housing 12 the pressure inside the bellows increases. At about 2 cm $H_2O$ pressure the pop-off valve 18 opens so that the excess exhaled gas is vented to the ambient.

The appropriate size or capacity of the bellows for adult patients is about 1500 milliliters (ml) whereas for small children or smaller animals a smaller bellows capacity, e.g. 300 ml, is needed. One commercially available ventilator is provided with a small bellows and bellows housing that can be substituted for the standard adult larger ones. A small bellows holder is seated on top of the adult bellows base. The housings are alternately mountable to the base using a large annular rubber piece seal. The large U-shaped cross section is designed to seal against the molded and irregular surface of the plexiglass housings, which seal tends to leak and to lack great reliability. It also tends to bind at disassembly. This ventilator construction also has the disadvantage that when the pediatric bellows holder is mounted in place, the adult bellows cannot be used, and the pediatric bellows holder must be removed to mount and use the large bellows. In that commercial ventilator the housings each have a square flange and four bolts to secure them to the base, making disassembly and exchange additionally complicated and time consuming.

Another well known commercial ventilator has a wire cage that is fitted over the bellows housing and attached to the base to firmly mount and seal the housing to the base. No provision is made for a small pediatric bellows. A later model of that exclusively adult ventilator provides a housing with four protruding pins close to the lower rim and a retainer ring which·has a flange for fitting over the pins to secure the housing. The edge of the flange engages three protruding screws integral with the base. To mount this molded plexiglass housing, it is pushed downward to seal against a large annular U-shaped rubber piece, as in the ventilator described above. The ring is fitted over the housing engaging the housing pins. Then the ring is oriented to allow the screw heads to fit through notches provided therefore in the ring flange. The ring is then twisted to secure the ring and thus the flange to the base.

It is an object of this invention to provide a pulmonary ventilator kit capable of being simply and quickly assembled with a large or small bellows and a corresponding large or small housing.

It is a further object of this invention to provide such a ventilator kit wherein said large and small housings are each mountable and reliably sealable to the same peripheral region of the base.

It is yet a further object of this invention to provide a small bellows adaptor capable of being easily fitted and reliably sealed to the base and which adaptor may be locked securely and safely in position by the mounting of the small housing.

SUMMARY OF THE INVENTION

A pulmonary ventilator-bellows-assembly kit includes a base with a cylindrical thin walled main-bellows-mounting portion first extending upwardly and further flaired outwardly from a top surface of the base. A cylindrical main bellows has an open end for being fitted and sealed over the flaired part of the main-bellows-mounting portion of the base. A cylindrical main housing has an open bottom portion that can be mounted to the base at a peripheral portion thereof to enclose the main bellows. An annular thin-walled small-bellows adaptor can be inserted, seated and sealed to the base within the annular main-bellows-mounting portion of the base. A small cylindrical bellows is provided that can be fitted and sealed over the adaptor. For use with the small bellows there is a small cylindrical housing of smaller diameter than the main bellows but adapted to be mounted and sealed to the very same peripheral base region to which the main housing is mountable.

One advantageous feature of the above described construction is the mounting position and small size of the small-bellows adaptor. This feature allows it to be installed although not used when the main bellows and main housing are mounted and in use. Thus the adaptor may always be in position for use when a small bellows and small housing will be substituted for the main bellows and main housing, respectively.

Another advantageous feature of this construction is the capability of the main and small housing for mounting and sealing at the same peripheral portion of the base. This simplifies construction which is particularly notable for the preferred housing mounting and sealing structure wherein the base has a circular raised portion at the base periphery with an O-ring fitted into a groove in an outer surface of the raised base portion. The inside diameter of the main housing and the inside diameter of an outwardly extending bottom portion of the small housing are such that either may be slipped over the raised base portion to seal against the O-ring. Each housing has at least two separate outwardly protruding knobs by which a twisting of the housing a few degrees locks the housing knobs in bayonet type receptacles on the base.

Yet another advantageous feature in the preferred structure of this invention includes an O-ring seal between the adaptor and the main-bellows-mounting portion of the base and the adaptor is locked in place when the small housing is mounted by the inward extending bottom portion thereof contacting a top portion of the adaptor. This construction has the additional advantage that the small housing cannot be locked to the base until the adaptor is properly seated and sealed, preventing the potentially dangerous condition that an improperly installed adaptor would allow leakage between the bellows-driving gas and the ventilating gas.

BRIEF DESCRIPTION OF THE DRAWINGS

FIG. 1 shows a diagram of a pulmonary ventilation system of the prior art.

FIG. 2 shows in exploded perspective view a ventilator assembly of this invention with a main (adult size) bellows and a large housing.

FIG. 3 shows in exploded perspective view a ventilator assembly of this invention with a small (pediatric size) bellows and a small housing.

DESCRIPTION OF THE PREFERRED EMBODIMENT

Figure 4:
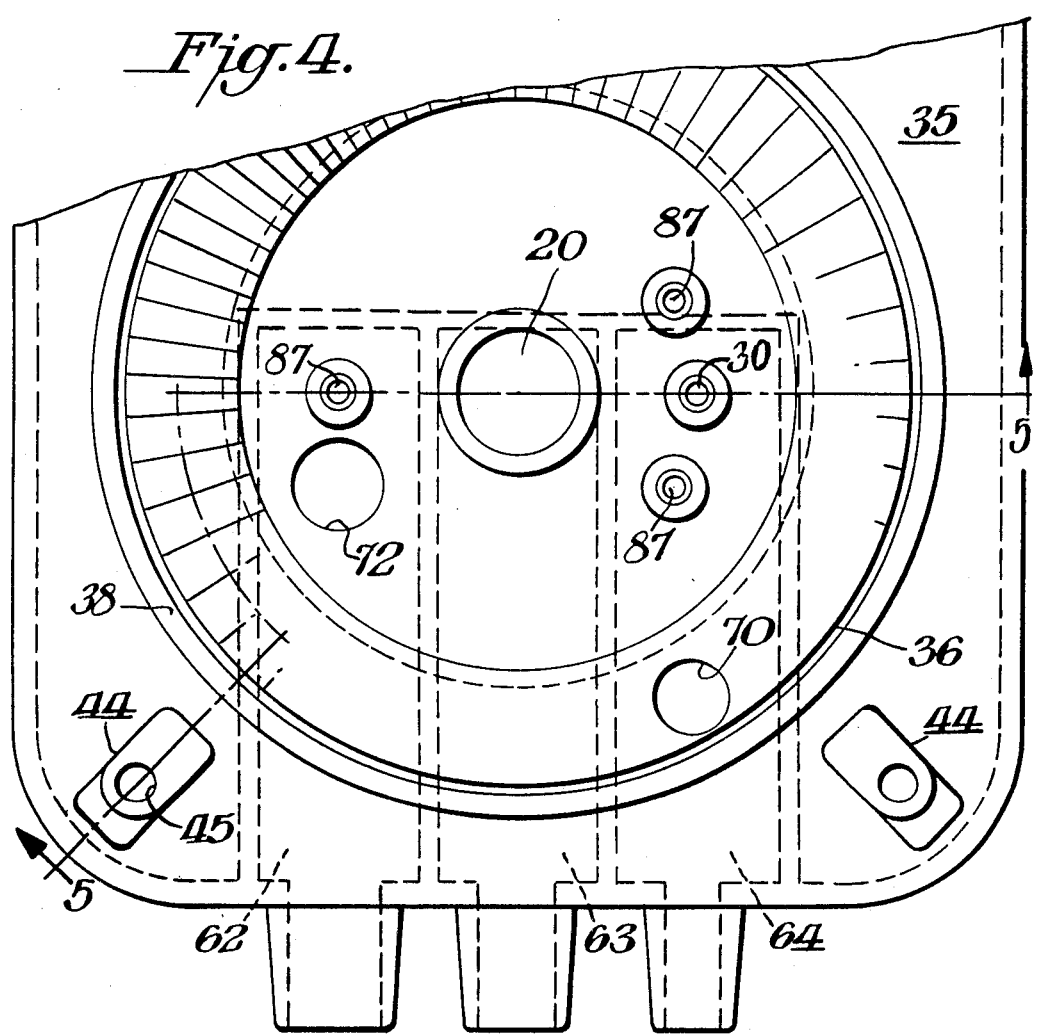
FIG. 4 shows in top view a portion of a base for a ventilator assembly kit of this invention.

Major parts of a pulmonary ventilator assembly of this invention for use with an adult subject, shown in the exploded view of FIG. 2, include a base 35, a main bellows 37 and a main housing 39. An annular main-bellows-mounting portion 36 of base 35 extends upwardly and flairs outwardly from the top surface of the base 35, the flaired portion being visible in FIG. 2.

The open bottom part of the main bellows 37 may be stretched and fitted to seal over the flaired portion of mounting portion 36. The housing 39 may be mounted over the main bellows 37 to the base mounting ring 38 sealing against a rubber O-ring 40 and locking to the base by twisting a few degrees in a counter clockwise direction to insert the housing knobs 42 into the bayonet type recepticles 44 at each of the four corners of the base 35.

The housing 39 is made of the high temperature transparent polyetherimide thermoplastic, ULTEM 1000, a Trademark of General Electric Company. It has a heat deflection temperature of about 200° C. at 264 p.s.i. and does not distort or degrade when subjected to sterilizing steam. The inner bottom portion of housing 39 is lightly machined to a smooth predetermined diameter for a precise mating and sealing against the O-ring 40. The top of the housing 39 is closed. A scale 46 is mounted to the housing 39 by which an observer may determine the amount of gas that has just been forced into the patient's breathing system by aligning the top of main bellows 37 with the volume scale 46.

A small-bellows-mounting adaptor 48 is shown seated in the base 35 in FIG. 2 for storage therein and ready access when the assembly is to be changed for use with a smaller, pediatric size or small-animal size bellows.

Such a small bellows 50 is shown in FIG. 3 which may be fitted and sealed over the outwardly flaired portion 52 of the adaptor 48.

The small housing 54 may be mounted over the small bellows 50. An enlarged open bottom portion 56 of the small housing, also cylindrical, has the same machined inside diameter as that of the main housing 39 and thus may be mounted and sealed at O-ring 40 to the same peripheral portion of base 35 as was the large housing 39. Also, the small housing 54 has knobs 58 that may be inserted into the same bayonet receptacles 44 for locking the small housing 54 to the base 35.

The portion of the base 35 that is shown in FIG. 4 except for the bayonet receptacles 44 that may be bonded to the molded base 35 is a single piece of plastic having been injection molded and subsequently precisely machined in the groove 60 in the base mounting ring 38 in which the O-ring 40 is retained.

Figure 5:
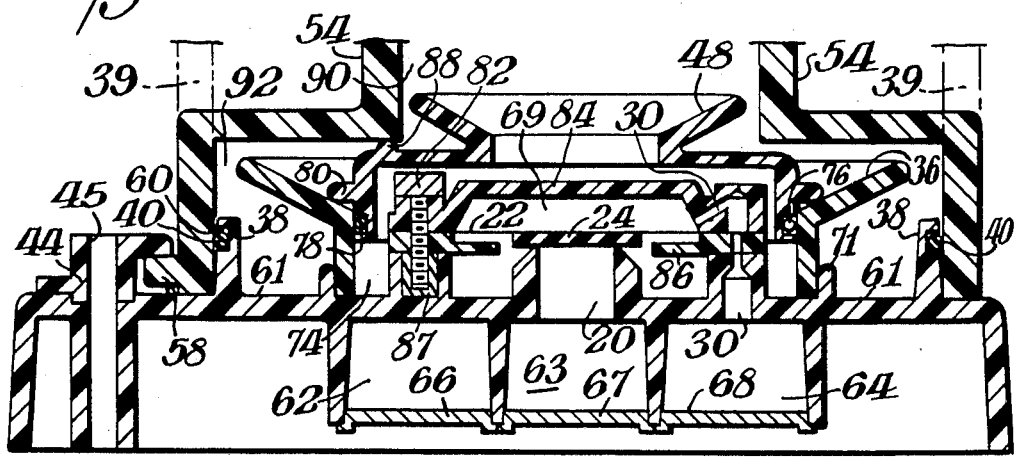
FIG. 5 shows in side sectional view, taken in plane 5—5, the base of FIG. 4 with in addition the small-bellows adaptor installed and a portion of a mounted housing.

Under the top surface 61 of the base 35 as seen in FIG. 5 three pneumatic passages 62, 63 and 64 are formed by bonding into place passage covers 66, 67 and 68, respectively. These passages are large and introduce little resistance to the gasses flowing therethrough.

The upwardly extending and outwardly flaired main bellows mounting portion of the base 35 is a thin-walled annular piece 36 that was separately injection molded and permanently bonded to the first noted base piece registered just inside the raised bonding ring 71 of base 35.

Major parts making up the pop-off valve in FIG. 5 are given the same numeral designations as in the pop-off valve 18 in FIG. 1. Thus exhaust port 20 leads directly to passage 63. The hole 30 in FIG. 5 connects the chamber 60 over the silicone rubber diaphram 22 with the drive gas passage 64 which is also connected through the hole 70 in the base 35 (See FIG. 4) to the drive chamber 90 formed between the housing 39 or 54 and the bellows (37 or 50). A hole 72 in base 35 connects the chamber 74 and the space within the bellows (37 or 50) with the breathing passage 62 that will be piped to the patient's breathing system. The valve seat 24 is made of an acetal resin, DELRIN made by Dupont E. I. deNemours & Co.

The small-bellows adaptor 48 is a thin walled plastic piece that may be most conveniently made by bonding together two injection molded plastic pieces (not shown separately). In the lower upwardly extending portion of adaptor 48, a small O-ring 76 is held in a groove 78 so that the adaptor 48 is sealed against the inner wall of the main-bellows-mounting base-portion 36. Also an outwardly protruding portion 80 of the adaptor 48 stops the adaptor 48 against the upper flaired portion of adaptor 48.

The pop-off valve may be completely disassembled for replacing the diaphram 22 or for cleaning by removing the adaptor 48, unscrewing the threaded bolts 82 (three places), and lifting off the plastic cap 84 and plastic ring 86. Bolts 82 are screwed into metal inserts 87 that are molded into the base 35.

A representative bottom portion of the small housing 54 is shown in FIG. 5 sealed against the O-ring 40 and seated against the surface 61 of the base 35. One of the knobs 58 is shown locked into one of the bayonet type recepticles 44 in FIG. 5. Recepticles 44 may be bonded to the base 35 or bolted through the hole 45 extending through base 35 and recepticle 44. The same bolts (not shown) may also serve to connect base 35 to a horizontal platform. When the small housing 54 is mounted, as shown, the horizontal portion of housing 54 contacts bumps 88 formed in the shoulder portion of the adaptor 48 so that the adaptor 48 is safely locked into its intended seated and O-ring position. But a gap between the bumps 88 insures pneumatic access between the chamber 90 on the one hand interior to housing 54 and exterior to the small bellows (50) and on the other hand the chamber 92 between the bottom portion of the small housing 54 and the adaptor. This adaptor-locking feature is not necessary when the large bellows and housing are mounted to the base (FIG. 3) since in that case the adaptor is not functional but is only stored there.

Not only are the housings 39 and 54 made of the high temperature ULTEM, but so are all the other injection molded plastic parts; 35, 34, 48, 84, 86, 66, 67 and 68. Those plastic parts are steam sterilizable as are the DELRIN valve seat 24, the silicone rubber diaphram 22 and the few metal parts, e.g. 82 and 87.

This ventilator also provides a large driving gas passageway 64 and large breathing gas passages 63 and 62 that insert little resistance to gas movement and are readily accessable for sterilizing and/or cleaning.

What is claimed is:

1. A pulmonary ventilator-bellows assembly kit comprising:
    (a) a base adapted for being supported on a horizontal platform, said base having an annular main-bellows-mounting portion extending upwardly from a top surface of said base;
    (b) a substantially cylindrical main bellows, the open end thereof adapted for being fitted and sealed to said bellows-mounting portion of said base;
    (c) a cylindrical main housing having a closed top portion and open bottom portion, said housing being adapted for mounting and sealing to a peripheral region of said base, and for enclosing said main bellows when said main bellows is fitted to said main-bellows-mounting portion of said base;
    (d) an annular thin-walled small-bellows adaptor that is adapted for being inserted, seated and sealed to said base within said annular main-bellows-mounting portion;
    (e) a substantially cylindrical small-bellows the open end thereof being adapted for being fitted and sealed to said small bellows adaptor; and
    (f) a small housing having a closed cylindrical top portion of smaller diameter than that of said main housing, and an enlarged open bottom portion having an inside diameter equal to that of said main housing adapted for mounting and sealing said small housing to said base peripheral region and, for enclosing and locking in place said small bellows when said adaptor is mounted and sealed to said base and said small bellows is fitted to said adaptor.

2. The kit of claim 1 wherein a middle portion of said annular thin-walled adaptor extends part-way inwardly from the lower portion thereof and an upper portion thereof flares upwardly and outwardly to accommodate said fitting of said small bellows, the rim of said flaired upper adaptor portion having a smaller diameter than that of said bottom adaptor portion so that a peripheral top surface part of said middle adaptor portion is unencumbered from the top.

3. The kit of claim 2 wherein a middle shoulder portion of said housing extends radially and horizontally inward from said bottom enlarged portion to said smaller top portion and is adapted to make contact at said middle portion of said small housing to said peripheral top surface part of said adapter to lock said inserted adaptor in place.

4. The kit of claim 3 additionally comprising a spacing means for providing a space between said contacting small-housing-middle portion and said peripheral surface part of said adaptor and for providing pneumatic access between the chambers formed on the one hand between the bottom portion of said small housing and said adapter and on the otherhand between the upper portion of said small housing and said small bellows.

5. The kit of claim 2 wherein said small bellows adaptor that is adapted for being sealed includes a rubber O-ring fitted in a groove formed in an outer surface of a lower portion thereof for contacting and sealing against the inner wall of said main bellows mounting portion.

6. The kit of claim 5 wherein said small bellows adaptor that is adapted for being seated includes at said lower portion thereof and above said groove an outwardly protruding part for seating against said flared portion of said adaptor.

7. The kit of claim 1, wherein said base has a bellows exhaust-hole about concentric with said annular main bellows-mounting portion of said base surface and extending through said base.

8. The kit of claim 7 additionally comprising a pop-off valve means mounted to said base over said exhaust hole for covering and closing said exhause hole when the pressure within the outer chamber between said main bellows and main housing or between said small bellows and small housing is at least as great as the ambient pressure in said exhaust hole, and for opening said exhaust hole when the pressure within said main bellows or said small bellows is about 1 cm of water greater than the ambient pressure in said exhaust hole.

9. The kit of claim 8 wherein said base has a driving-gas hole extending through said base from said base surface between said peripheral portion and said main bellows mounting portion to provide access to said outer chamber; and a pulmonary-gasses hole extending through said base from said base surface between said pop-off valve means and said main bellows-mounting portion of said base to provide pneumatic access to the chamber within said bellows.

10. The kit of claim 1 wherein said base has a circular raised portion at said peripheral base region having an outside diameter about equal to the inside diameter of said main housing at a bottom portion thereof, the inside diemater of said small-housing bottom portion being equal to that of said main housing, a rubber O-ring being fitted in a groove formed in the outer surface of said raised portions so that either of said housings may be mounted and sealed to said base by pushing said open bottom housing portion downward and about said raised base portion.

11. The kit of claim 10 wherein the base mountable bottom-portions of said main and of said small housings include at least two separate outwardly protruduing knobs and said kit additionally comprises a bayonet-type housing-locking means for locking either of said housings to said base by said knobs when said either housing is mounted to said base and rotated a few degrees relative thereto.

12. A pulmonary-ventilator-bellows assembly kit comprising:
(a) a base adapted for being supported on a horizontal platform, said base having an exhaust orifice in a top surface thereof and a cylindrical thin-walled portion extending upwardly from said top base surface and located about concentrically about said exhaust orifice, said cylindrical thin-walled portion having an outwardly flaired upper rim;
(b) a substantially cylindrical main bellows the open end thereof adapted for being mounted and sealed to said flaired rim portion;
(c) a main cylindrical housing having a closed top portion and an open bottom portion, said bottom portion adapted for mounting and sealing to said base and for enclosing said main bellows within said main housing and base when said main bellows is mounted to said thin walled base portion;
(d) a cylindrical thin-walled small-bellows adaptor having an outside diameter about equal to the inside diameter of said cylindrical thin-walled base portion and adapted for being fitted into said base portion and sealed thereto; said adaptor having an outwardly flaired open rim portion of substantially smaller diameter than that of said upward extending base region;
(e) a substantially cylindrical small bellows having an open end adapted for being mounted and sealed to said flaired rim portion; and
(f) a small cylindrical housing having a closed top portion of smaller diameter than that of said main housing and an enlarged open lower portion adapted for mounting and sealing to said base, for enclosing said small bellows within said small housing and base when said small bellows adaptor is fitted to said base and said small bellows is mounted to said adaptor, and for locking said small bellows adaptor in place.

* * * * *